(12) United States Patent
Shih et al.

(10) Patent No.: US 7,458,265 B2
(45) Date of Patent: Dec. 2, 2008

(54) PIEZOELECTRIC CANTILEVER SENSORS

(75) Inventors: Wan Y. Shih, Bryn Mawr, PA (US);
Wei-Heng Shih, Bryn Mawr, PA (US);
Zuyan Shen, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 10/595,570

(22) PCT Filed: Oct. 27, 2004

(86) PCT No.: PCT/US2004/036705

§ 371 (c)(1),
(2), (4) Date: Jul. 24, 2006

(87) PCT Pub. No.: WO2005/043126

PCT Pub. Date: May 12, 2005

(65) Prior Publication Data

US 2007/0089515 A1      Apr. 26, 2007

Related U.S. Application Data

(60) Provisional application No. 60/514,803, filed on Oct. 27, 2003.

(51) Int. Cl.
*G01N 5/04* (2006.01)
*G01N 25/08* (2006.01)

(52) U.S. Cl. .................. 73/579; 73/73; 73/61.75; 73/580

(58) Field of Classification Search ........... 73/579, 73/24.01, 64.53, 61.75, 73, 61.49, 580
See application file for complete search history.

(56) References Cited

U.S. PATENT DOCUMENTS 5,079,199 A      1/1992   Ochi et al.

(Continued)

OTHER PUBLICATIONS

Shih, Wan Y. et al, Simultaneous Liquid Viscosity and Density Determination with Piezoelectric Unimorph Cantilevers, Journal of Applied Physics, Jan. 15, 2001, pp. 1497-1505, vol. 89, No. 2, American Institute of Physics, USA.

(Continued)

*Primary Examiner*—Hezron E. Williams
*Assistant Examiner*—Jacques M. Saint-Surin
(74) *Attorney, Agent, or Firm*—Knoble, Yoshida & Dunleavy LLC

(57) ABSTRACT

A piezoelectric cantilever with a non-piezoelectric, or piezoelectric tip useful as mass and viscosity sensors. The change in the cantilever mass can be accurately quantified by monitoring a resonance frequency shift of the cantilever. For biodetection, antibodies or other specific receptors of target antigens may be immobilized on the cantilever surface, preferably on the non-piezoelectric tip. For chemical detection, high surface-area selective absorbent materials are coated on the cantilever tip. Binding of the target antigens or analytes to the cantilever surface increases the cantilever mass. Detection of target antigens or analytes is achieved by monitoring the cantilever's resonance frequency and determining the resonance frequency shift that is due to the mass of the adsorbed target antigens on the cantilever surface. The use of a piezoelectric unimorph cantilever allows both electrical actuation and electrical sensing. Incorporating a non-piezoelectric tip (14) enhances the sensitivity of the sensor. In addition, the piezoelectric cantilever can withstand damping in highly viscous liquids and can be used as a viscosity sensor in wide viscosity range.

43 Claims, 7 Drawing Sheets

U.S. PATENT DOCUMENTS

| | | | |
|---|---|---|---|
| 5,162,691 | A | 11/1992 | Mariani |
| 5,283,037 | A * | 2/1994 | Baer et al. ............... 422/82.01 |
| 5,719,324 | A | 2/1998 | Thundat |
| 5,742,377 | A | 4/1998 | Minne |
| 5,883,705 | A | 3/1999 | Minne |
| 6,252,335 | B1 | 6/2001 | Nilsson |
| 6,289,717 | B1 | 9/2001 | Thundat |
| 6,336,366 | B1 | 1/2002 | Thundat |
| 6,545,273 | B1 | 4/2003 | Singh |
| 6,813,815 | B2 * | 11/2004 | Namerikawa et al. ...... 29/25.35 |
| 7,061,166 | B2 * | 6/2006 | Kuniyasu .................... 310/365 |
| 7,089,813 | B2 * | 8/2006 | Takeuchi et al. .............. 73/865 |
| 7,262,546 | B2 * | 8/2007 | Namerikawa et al. ....... 310/366 |
| 7,329,536 | B2 * | 2/2008 | Zeng et al. ............... 435/287.2 |
| 2005/0248235 | A1 * | 11/2005 | Namerikawa et al. ....... 310/328 |
| 2006/0123910 | A1 * | 6/2006 | Cunningham et al. ......... 73/580 |
| 2007/0089519 | A1 * | 4/2007 | Hao et al. ..................... 73/649 |
| 2008/0035180 | A1 * | 2/2008 | Mutharasan et al. .......... 134/32 |

OTHER PUBLICATIONS

Yi, Jeong Woo et al., Effect of Length, Width, and Mode on the Mass Detection Sensitivity of Piezoelectric Unimorph Cantilevers, Journal of Applied Physics, Feb. 1, 2002, pp. 1-7, vol. 91, No. 3, American Institute of Physics, USA.

Yi, Jeong W. et al., In Situ Cell Detection using Piezoelectric Lead Zirconate Titanate-Stainless Steel Cantilevers, Jan. 1, 2003, pp. 619-625, vol. 93, No. 1, American Institute of Physics, USA.

Thaysen, J. et al., Cantilever-Based Bio-Chemical Sensor Integrated in a Microliquid Handling System, 2001, pp. 401-404.

L, Junjun et al., Micromachined Biomimetic Sensor Using Modular Artificial Hair Cells, pp. 1-3.

Thaysen, J., Label Free Detection, BioMEMs Materials and Fabrication Methods, Track 2, 3:00pm, Sep. 7, 2002, pp. 1-3.

Lee, Chengkuo et al., Self-Excited Piezoelectric PZT Micorantilevers for Dynamic SFM—With Inherent Sensing and Actuating Capabilities, Sensors and Actuators A72, 1999, pp. 179-188.

Huiming Gu et al., Single-Calcination Synthesis of Pyrochlore-Free 0.9Pb(Mg 1/3NB2/3)O3-0. 1PbTiO3 and Pb (Mg1/3Nb2/3)O3 Ceramics Using a Coating Method, Journal of the American Ceramic Society, 2003, pp. 217-221, vol. 86, No. 2.

* cited by examiner

PIEZOELECTRIC CANTILEVER SENSORS

STATEMENT OF GOVERNMENT INTEREST

This invention was reduced to practice with Government support under Grant No. NAG2-1475 awarded by NASA, Grant No. R01 EB00720-01 awarded by NIH and Grant No. R-82960401 awarded by the EPA; the Government is therefore entitled to certain rights to this invention.

BACKGROUND OF THE INVENTION

1. Field of the Invention

The invention relates to the field of sensors. In particular the invention relates to methods and apparatus for sensing biological and chemical species, as well as the measurement of viscosity.

2. Description of the Related Technology

Most of the current work done with biosensing technologies relies on fluorescence, lasers, fiber-optics-based methods, quartz crystal microbalance technology, electrochemical enzyme immunoassays, and binding to metal particles. Most of these techniques are neither direct, nor quantitative. Many of these techniques are also quite slow. In addition, most of the aforementioned techniques do not lend themselves to measurement of changes in mass, which may provide a convenient way to measure a variety of different parameters.

A mass sensor based on resonance frequency needs three components, an actuator (driver), a resonator, and a detector. A popular mass sensor is a silicon-based micro-cantilever due to its commercial availability and ease of integration with existing silicon based methodologies. In a silicon-based micro-cantilever mass sensor, the micro-cantilever acts as the resonator and is driven by an external lead zirconate titanate (PZT) actuator at the base of the micro-cantilever to generate vibrations in the resonator, which may be detected by an external optical detector. For bio-detection, receptors are immobilized at the micro-cantilever surface. Binding of antigens to the receptors immobilized on the cantilever surface increases the cantilever mass and causes a decrease in the resonance frequency. Detection of target molecules is achieved by monitoring the mechanical resonance frequency. In spite of the popularity of silicon-based micro-cantilevers, they rely on complex external optical components for detection. In addition, the PZT vibration driver adds to the weight and complexity of the sensor. Further, the external actuator can only be located at the base of the micro-cantilever, which greatly limits its effectiveness in driving the cantilever's vibration. The optical means of detection also limits how small the micro-cantilever can be fabricated, and therefore limits the mass detection sensitivity.

In addition to mass detection, silicon-based micro-cantilevers have also been used as sensors for small molecules by detecting the stress generated on the cantilever by the adsorption of species onto receptors associated with the cantilever. Antibody or DNA receptors are coated on the surface of the micro-cantilevers to bind target protein or DNA molecules. The stress generated at the time of binding or unbinding of the target molecules to the receptors on the micro-cantilever surface induces a temporary deflection of the micro-cantilever that may be detected by external optical components or by an adsorption-stress-induced DC voltage on a piezo-resistive coating layer on the cantilever surface. Because the binding-induced stress decays with time, it can only be detected when the micro-cantilever is first introduced to the target molecules. The induced stress, and hence the induced DC voltage, dissipates within 20 minutes. Also, detecting the adsorption-induced stress in this manner offers no information about the amount of target antigen adsorbed on the cantilever.

Moreover, immersing silicon-based micro-cantilevers in water reduces the resonance intensity by an order of magnitude, reducing the Q factor, defined as the ratio of the resonance peak frequency relative to the resonance peak width at half peak height, to about one, thus making it impractical to use silicon-based micro-cantilevers for in-water detection. The main reason that such silicon-based micro-cantilevers do not exhibit sufficiently high resonance signals in water is that silicon-based micro-cantilevers are not piezoelectric. The deflection at the tip of the silicon-based cantilever is driven by the vibration driver located at the base of the silicon-based cantilever and is detected by external optical components. Driving a cantilever at its base is not the most effective way to generate deflections at the tip of the cantilever. While the relatively weak deflection signal generated by the vibration driver at the base is sufficient for in-air detection it does not withstand the damping of water.

Silicon-based micro-cantilever sensors therefore have the following shortcomings when used for mass detection using the resonance mechanism: (1) A silicon-based micro-cantilever sensor needs to be driven by an external actuator. (2) A silicon-based micro-cantilever sensor loses its detection sensitivity in water due to viscous damping. (3) A silicon-based micro-cantilever requires a complex external optical detection system. The resolution of the optical detector puts a limit on how small the displacement can be and therefore, how small the cantilever can be, which places significant constraints on detection sensitivity.

For detection of stress, the silicon-based micro-cantilever sensor does not need a driver, but requires an external optical system or a piezo-resistive layer. Stress detection using a piezo-resistive layer involves DC electrical measurements. Furthermore, detection using a piezo-resistive layer is not very sensitive. Therefore, most silicon cantilevers use an external optical means for detection. In silicon-based micro-cantilevers, the adsorption induced stress decays in 20 minutes and the adsorbed amount cannot be quantified.

Compared to silicon-based sensors, piezoelectric micro-cantilever sensors are not as bulky and complex. Piezoelectric devices are excellent transduction candidates because of their short response time and high piezoelectric coefficients. Because they are piezoelectric, both the driving and sensing of the mechanical resonance can be conveniently done electrically within the resonator. Currently, piezoelectric biosensors are based on commercially available quartz crystal microbalances (QCM), a disk device that uses thickness-mode resonance for sensing. Although quartz is a weak piezoelectric material, it is widely used as a layer thickness monitor in part due to the availability of large quartz single crystals to make the membranes. The typical mass detection sensitivity of a 5 MHz QCM that has a minimum detectable mass density (DMD) of $10^{-9}$ g/cm$^2$ is about $10^{-8}$ g/Hz, about two orders of magnitude less sensitive than millimeter sized piezoelectric cantilevers. Moreover, because QCMs are larger in size, they are harder to develop into array sensors for multiple antigens. Quartz is a weak piezoelectric, much like the silicon-based cantilever, when immersed in water, the resonance peak intensity of QCM is reduced to less than one twentieth of the in-air peak intensity due to viscous damping of water, thus limiting the use of QCMs in water.

QCMs employ a piezoelectric crystal that serves as the actuator, resonator, and detector. However, it involves shear waves of the thickness mode of the crystal rather than the flexural mode of the cantilever geometry. QCMs have a lower mass sensitivity than a silicon-based micro-cantilever. QCMs are also limited by the following shortcomings. Due to its planar geometry, for mass detection, QCMs are not capable of detecting very small amounts of mass, which limits the detection sensitivity. Also, QCMs use higher resonance frequencies (>5 MHz), which reduces the relative sensitivity, ($\Delta f/f$), where f and $\Delta f$ denote the initial resonance frequency and the resonance shift. QCMs are also difficult to miniaturize in order to improve the detection sensitivity.

Comparing the two direct biosensor technologies, silicon-based-micro-cantilever sensors[1], exhibit high mass-detection sensitivity, but the optical detection system is large and complex. QCM-based sensors have the merit of simple electrical driving and electrical detection but they exhibit a much lower mass sensitivity than silicon-based micro-cantilevers.

QCMs are also larger in size thus harder to develop into array sensors for multiple antigens.

Therefore, there exists a need for improvement of the sensing capabilities of existing sensors.

SUMMARY OF THE INVENTION

In a first aspect, the present invention relates to an apparatus for sensing mass having a non-piezoelectric layer, and a piezoelectric layer bonded to the non-piezoelectric layer. The length of one of the layers is less than the length of the other of the layers. The apparatus also has electrodes located proximate to the piezoelectric layer.

According to a second aspect of the invention, a method for the detection of mass is provided. The method involves the steps of providing an apparatus having a non-piezoelectric layer, and a piezoelectric layer bonded to the non-piezoelectric layer, wherein the length of one of the layers is less than the length of the other of the layers, measuring a resonance frequency of the apparatus and comparing the measured resonance frequency to a baseline to determine a resonance frequency shift.

According to a third aspect of the invention, a method for measuring viscosity is provided. The viscosity measurement method involves the initial step of providing an apparatus having a non-piezoelectric layer, and a piezoelectric layer bonded to the non-piezoelectric layer, wherein the length of one of the layers is less than the length of the other of the layers. The apparatus also includes electrodes located proximate to the piezoelectric layer. The method also involves the steps of placing the provided apparatus in a liquid, measuring a resonance frequency of the apparatus, comparing the resonance frequency to a baseline to determine a resonance frequency shift, and determining a viscosity of the liquid based upon the resonance frequency shift.

These and various other features and advantages that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described embodiments of the invention.

DETAILED DESCRIPTION OF THE PREFERRED EMBODIMENT(S)

Piezoelectric cantilever sensors (PECS) provide rapid, direct, and quantitative bio-detection. PECS combine the merits of silicon based sensors and QCMs and (i) exhibit high detection sensitivity, (ii) use electrical means for driving and sensing, (iii) have a minimal damping effect, and (iv) are compact, light-weight, and simple to operate. A PECS can be used in water for biological or chemical sensing. A PECS can also be used in oil or other highly viscous fluids for chemical and viscosity sensing.

Figure 1:
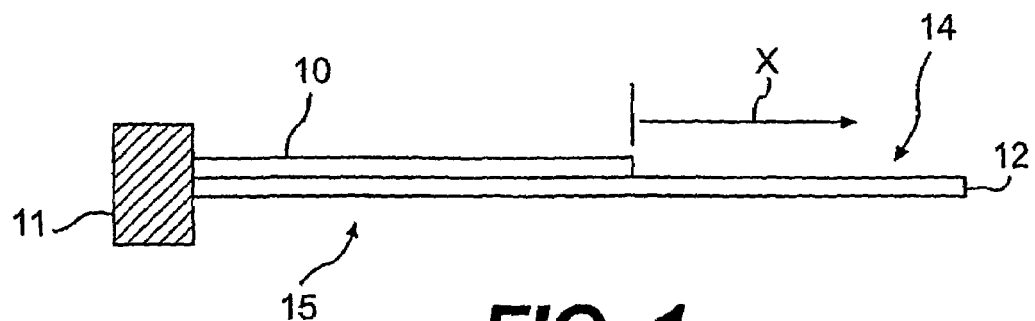
FIG. 1 shows a diagram of a piezoelectric cantilever sensor.

An important aspect of the present invention involves the detection mechanism employed in the device of the invention, as well as the placement of the actuator. Detection using PECS 15, shown in FIG. 1, is achieved electrically using the piezoelectric layer, while detection by a silicon-based micro-cantilever is achieved by optically monitoring the resonance frequency shift. The driver of the PECS 15 is the same as the resonator in PECS 15, which facilitates the most effective driving, whereas the external driver of a silicon-based micro-cantilever sits at the base of the cantilever, which makes the driving less effective.

Piezoelectric cantilever sensors may be used as mass detectors for bio-detection applications and chemical detection applications. FIG. 1 shows a general diagram of how a PECS 15 is constructed. PECS 15 is a piezoelectric unimorph cantilever with a piezoelectric layer 10 bonded to a longer non-piezoelectric layer 12. Both piezoelectric layer 10 and non-piezoelectric layer 12 are attached to clamp 11. The portion of non-piezoelectric layer 12 that extends beyond the end of piezoelectric layer 10 forms a non-piezoelectric tip 14. Alternative embodiments may have piezoelectric layer 10 extend beyond non-piezoelectric layer 12 and, in such alternative embodiments a piezoelectric tip (not shown) would be formed. In order to achieve the best results one of the piezoelectric and non-piezoelectric layers must extend beyond the other.

Figure 2:
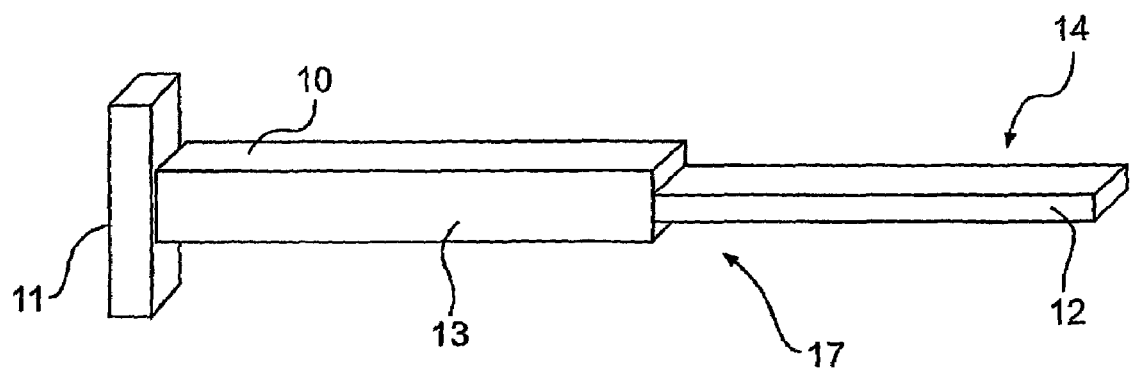
FIG. 2 shows a diagram of an alternative embodiment of the cantilever sensor having two piezoelectric layers.

FIG. 2 shows a diagram of an alternative embodiment of the cantilever sensor 17 having two piezoelectric layers 10 and 13. In this embodiment, non-piezoelectric layer 12 is placed between piezoelectric layers 10 and 13. In alternative embodiments, it is also possible to have a piezoelectric layer placed between two non-piezoelectric layers, if desired.

An important aspect of the current invention lies in the use of a highly piezoelectric layer as part of the cantilever structure, which enables electrical means for detection and actuation within the cantilever. Piezoelectric material produces electricity via mechanical pressure on certain crystals (notably quartz or Rochelle salt); or, alternatively, electrostatic stress produces a change in the linear dimensions of the crystal. Some advantages of the present invention include allowing simple electrical measurements for detection with better signal sensitivity compared to silicon-based micro-cantilevers. This is clearly evidenced in Q values, where $Q=f/\delta f$ with f representing the resonance frequency and $\delta f$ the width of the resonance peak at half the peak height. A higher Q represents a better signal intensity. PECS 15 has a Q value well above 50 in water, whereas silicon-based micro-cantilevers have a Q value of about 1 in water.

In addition, using electrical measurements for detection does not impose a limit on how small the cantilever can be. This allows the cantilevers to be miniaturized to further improve the mass detection sensitivity. For example, by miniaturizing cantilevers to smaller than 50 μm long, the mass detection sensitivity can reach $10^{-15}$ g/Hz. The piezoelectric layer 10, which is the driver, is part of the cantilever. Because the driver of a PECS 15 is also the resonator, it leads to more effective actuation and better signal intensities for detection. This is very different from the external PZT actuator used in a silicon-based micro-cantilever that sits at the base of the cantilever. Driving a cantilever from the base of the cantilever is the most ineffective way to drive a cantilever (This is analogous to bouncing off a diving board from the base rather than from the tip).

PECS 15 uses AC electrical impedance measurements to detect the resonance frequency shift, whereas the silicon-based-micro-cantilever uses optical means for detection. Some silicon-based micro-cantilevers use a piezo-resistive layer to measure a DC voltage induced by the stress generated by the adsorption. This is different from the AC impedance measurements used by PECS 15 for monitoring the resonance frequency shift. Moreover, cantilevers with a piezo-resistive layer do not provide the same level of signal intensity as cantilevers with a highly piezoelectric layer, as in the present invention.

The differences between PECS 15 and QCM are just as striking. PECS 15 uses a flexural (bending) mode resonance for detection rather than the thickness mode, thereby employing a much lower frequency and thus having a higher sensitivity. The flexural mode resonance frequency is typically below 100 kHz. In contrast, the thickness mode resonance frequency of QCM is typically above 5 MHz. The lower frequencies used by PECS 15 allows a better resolution in frequency. For the same amount of frequency shift, $\Delta f$, the relative frequency change $\Delta f/f$ is higher with PECS 15 than with QCM. Due to the planar geometry of the QCM, a QCM cannot detect very small masses. The piezoelectric coefficient of quartz is two orders of magnitude smaller than PZT. This results in a smaller signal intensity, which makes QCM unfavorable for in-water detection.

Detection is achieved by monitoring the cantilever's resonance frequency shift due to the mass increase of, for example, an adsorbed target antigen on cantilever tip 14, using electrical means. The use of the highly piezoelectric layer facilitates the all-electrical actuation and monitoring of the resonance frequency shift. With, for example, an antibody immobilized at the cantilever tip, piezoelectric unimorph cantilever sensors with a tip permit rapid, direct, quantitative detection of bioagents such as proteins and cells in water with simple all electrical measurements.

Furthermore, as noted above, using electrical measurements for detection allows the use of very small cantilevers, for example, cantilevers 50 μm long can be used to achieve unprecedented mass detection sensitivity. A 50 μm long cantilever can detect masses on the order of femtograms.

The design of the non-piezoelectric tip of the cantilever contributes to the detection sensitivity and versatility: (1) by increasing the adsorption area for detection, (2) by amplifying the vibration amplitude at the tip to increase the mass detection sensitivity, and (3) by enhancing the intensity of the second and higher order resonance peaks to allow detection at higher order peaks (which in turn further increased the mass detection sensitivity). The result of the invention is a sensor that can be used to detect biological agents and/or chemical agents that can (1) sense and quantify mass, (2) directly detect the target antigen or chemical without labeling and amplification, (3) be used in an aqueous solution without reducing its Q factor, (4) both actuate and detect by electrical means, thereby enabling it to be portable, (5) be miniaturized to achieve unprecedented detection sensitivity e.g., $10^{-15}$ g/Hz (smaller than the mass of the single bacterium) and also be compatible with microelectronic circuitry, and (6) be able to withstand damping of highly viscous fluids such as oil for viscosity measurements and performing chemical sensing in oil or other viscous fluids.

The mass detection sensitivity of piezoelectric unimorph cantilevers with no tip (i.e. the tip length $L_2=0$) has been analyzed experimentally. Denoting $\Delta m$ as the adsorbed point mass at the cantilever free end, the frequency change, $\Delta f_i$, in the $i^{th}$-mode resonance frequency, $f_i$, due to the mass change, $\Delta m$, can be approximated as $$\Delta f_i = -f_i \Delta m/M_e, \quad (1)$$

where $M_e$ is the effective mass of the cantilever. The frequency change can be further related to the cantilever length, $L_p$, and width, w, as $$\Delta f_i/\Delta m \propto 1/wL_p^3. \quad (2)$$

The mass change per Hz is therefore $\Delta m/\Delta f_i \propto wL_p^3$, indicating that reducing the cantilever size by a factor $\alpha$, the mass change per Hz will decrease with the fourth power of $\alpha$ as $\Delta m/\Delta f_i \propto \alpha^4$. $\Delta m/\Delta f$ is expected to reach $10^{-15}$ g/Hz with a 50-μm long piezoelectric micro-cantilever with no tip, which allows the detection of a single particle of 60 nm in size; and $10^{-18}$ g/Hz with a 15 μm long piezoelectric micro-cantilever that makes detection of a single sphere of 10 nm in diameter or a single DNA molecule ($10^6$ Dalton) possible. With a tip of an optimal length and thickness, detection sensitivity is further enhanced.

Because PECS 15 utilizes mechanical resonance as the means for sensing, the ratio of the thickness ($t_n$) of the non-piezoelectric layer to the thickness ($t_p$) of the piezoelectric layer plays an important role. The optimal thickness ratio depends on the Young's modulus ratio of the two layers. Denoting the thickness and Young's modulus of the piezoelectric and non-piezoelectric layers as $t_p$, $E_p$ and $t_n$, En, respectively, and the thickness ratio ($t_n/t_p$) and Young's modulus ratio ($E_n/E_p$) as a and b respectively, the optimal resonance strength occurs at $a_{max}$ that satisfies $$1-2b-2ba_{max}^2-2ba_{max}^3-(4b+3b^2)a_{max}^4+3b^2a_{max}^5=0$$

for a fixed piezoelectric layer thickness and a varied non-piezoelectric layer thickness. For a fixed total thickness, the optimal thickness ratio occurs at $a_{max}=b^{-1/2}$. In practice, the optimal range of the thickness ratio, $a_{max}$, is from about 0.2 to about 1. A working range of the thickness ratio ($t_n/t_p$) is from about 0.1 to 3.

The length ratio influences the strength of higher-mode resonance peak intensity and detection sensitivity. The ratio $l_1/l_2$ for optimal high-mode intensity occurs around about $l_1/l_2=0.5$ where $l_1$ is the length of the section containing both the piezoelectric and non-piezoelectric layer and $l_2$ is the length of the layer that extends beyond the section containing both layers to form the tip, respectively. The length ratio ($l_1/l_2$) may range from about 0.2 to 2.

The resonance intensity of PECS 15 is also strongly influenced by the total thickness of the cantilever and more importantly by the piezoelectric layer thickness. This is because most highly piezoelectric layers are ceramic with high density and elastic modulus. For sensors with a total length 2 cm to 0.5 μm, the piezoelectric layer thickness, $t_p$, ranges from 250 μm to 0.5 μm. When piezoelectric layer thickness, $t_p$, ranges from 250 μm to 0.5 μm, the total cantilever thickness $t_p+t_n$ ranges from 350 μm to 1 μm.

Figure 3:
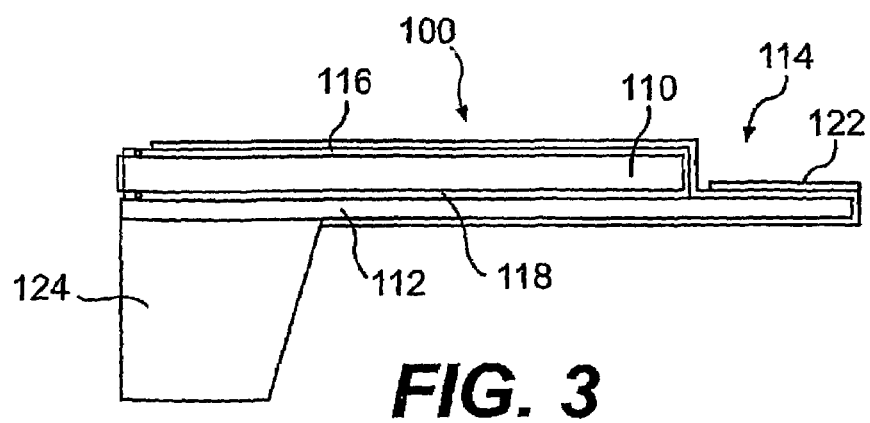
FIG. 3 shows a diagram of piezoelectric micro-cantilever sensor.

FIG. 3 shows a schematic of a micro-fabricated piezoelectric micro-cantilever sensor 100, which is a type of PECS 15. It is important to note that while the embodiment shown in FIG. 3 shows non-piezoelectric layer 112 being longer than piezoelectric layer 110 it is possible to have piezoelectric layer 110 be longer than non-piezoelectric layer 112 in order to form a piezoelectric tip. As shown in FIG. 3, Piezoelectric layer 110 and non-piezoelectric layer 112 are on the order of micron thicknesses. For example, lead zirconate titanate (PZT), lead magnesium niobate-lead titanate solid solutions ($PMN_{0.65}$-$PT_{0.35}$) and strontium lead titanate ($Sr_xPb_{1-x}TiO_3$) films can be used to form the highly piezoelectric layers 110. In FIG. 3, non-piezoelectric layer 112 is $Si_3N_4$. Other material choices for layer 112 include ceramics such as $SiO_2$ or metals such as copper, stainless steel, Ti, or polymers or the composites of ceramics, metals, or polymers. On top of piezoelectric layer 110 is top electrode 116, which can be made from Au/Cr or Pt/Ti or $SiO_2$. Top electrode 116 can be patterned into several regions. Bonding pad 122 is placed on the non-piezoelectric tip 114. Bonding pad 122, when used for bio-sensing, can be used to immobilize receptors to bind antigens, antibodies or DNA. Bonding pad 122 can also be made of other absorbent materials to absorb analytes for detection of various chemicals. It is also possible to use no bonding pad 122 an instead provide material for and use the non-piezoelectric tip for sensing the viscosity of fluids. Bonding pad 122 can be constructed from, for example, gold or $SiO_2$ and any other material appropriate for the type of detection.

Between piezoelectric layer 110 and non-piezoelectric layer 112 is bottom electrode 118, which can be constructed out of Pt/$TiO_2$ on $SiO_2$ or Pt/Ti on a metal substrate. On the bottom portion of non-piezoelectric layer 112 can be a layer of $Al_2O_3$ or other electrically insulating materials for electrical insulation of the electrodes. The base of non-piezoelectric layer 112 is placed on top of clamp 124, which can be constructed out of Si or glass or any substrate material. The thickness ratio between piezoelectric layer 110 and non-piezoelectric layer 112 is chosen such that it optimizes the resonance signal and the mass detection sensitivity. In alternative embodiments, piezoelectric micro-cantilever sensors (PEMS) 100 can be arranged into arrays using micro-fabrication techniques. The piezoelectric micro-cantilever sensor 100 can be utilized for in-situ rapid, simultaneous, direct quantification of molecules with unprecedented attogram ($10^{-18}$ g) sensitivity.

The possible resonance frequency for mass sensing ranges from 1 kHz to 10 MHz, to preferably 50 kHz to 5 MHz Using the resonance frequency shift to quantify the mass change of a piezoelectric micro-cantilever sensor 100 as a detection mechanism for biological systems has the advantages that (1) the post-adsorption resonance frequency change will remain unchanged as long as the adsorbed target antigens remain adsorbed, (2) the amount of the adsorbed antigens can be determined from the resonance frequency shift, and (3) it uses all-electrical actuation and detection. This is different from bio-detection using silicon-based micro-cantilevers with a piezo-resistive layer, which detects a DC voltage induced by the stress upon adsorption of the antigens.

As described above, miniaturization of the piezoelectric unimorph cantilevers to make piezoelectric micro-cantilever sensors (PEMS) 100 allows unprecedented mass detection sensitivity. Another benefit of piezoelectric micro-cantilever sensors (PEMS) 100 is the potential for reduction of detection time. The attachment of target bio-agents, or target substances requires diffusion of the target bio-agents to the surface PEMS 100. A smaller detectable mass change, Δm, means smaller amounts of bio-agents, or other substances, need to absorb on the PEMS 100 surface for detection, which is important for ultra-low concentration detection. A smaller minimal detectable amount means a smaller diffusion volume and therefore a shorter diffusion time for materials, to reach the cantilever surface. When the cantilever is shrunk by a factor of α in all dimensions, the time needed for the minimal detectable amount of material, to reach the surface of PEMS 100 is reduced by a factor $α^{4/3}$. For example, when cantilever size is reduced from 1 cm to 50 μm, the detection time is reduced by a factor of about 1000. Thus, reducing the cantilever size not only increases the sensitivity of the device, it may also significantly decrease the detection time.

Currently, with a 5-mm long cantilever, the detection time is about 60 minutes in a concentration of 1 g/L. With a cantilever 50 μm in length, the adsorption time may be significantly less than 1 minute, allowing for real-time concentration quantification.

It is to be understood that the geometry shown in FIG. 3 is only one of the possible geometries that the PEMS 100 could have. The shape of PEMS 100 can be full or open, rectangular, rounded, or various other polygonal shapes. Non-piezoelectric tip 114 can be an extension of non-piezoelectric layer 112, or could alternatively be constructed of a different, non-piezoelectric material than the non-piezoelectric layer 112. Furthermore, it is possible to have the piezoelectric layer be longer than the non-piezoelectric layer in order to form a piezoelectric tip. The length of piezoelectric layer 110 can range from 2.5 centimeters to 0.5 microns, or from 1.5 centimeter to 1.0 micron. The thickness of piezoelectric layer 110 can range from a 10 millimeters to sub-micron thickness', or from 1.0 millimeter to sub-micron thickness'. The width of the piezoelectric layer can range from 10 millimeters to 0.5 microns, or from 1.0 millimeter to 1.0 micron. The length of non-piezoelectric layer 112 can range from 2.5 centimeters to 0.5 microns, or from 1.5 centimeters to 1.0 micron. The thickness of non-piezoelectric layer 112 can range from 10 millimeters to sub-micron thickness', or from 1 millimeter to sub-micron thickness'. The width of the non-piezoelectric layer 112 can range from 10 millimeters to 0.5 microns, or from 1.0 millimeter to 1.0 micron. The PEMS 100 can be tapered in the lateral and/or thickness direction. Likewise, the non-piezoelectric tip can be tapered in the lateral and/or thickness direction, and can also be much narrower or thinner than the piezoelectric layer. Furthermore, the cantilevers, such as PEMS 100 can be extended into a sandwich design employing two piezoelectric layers 110 sandwiching a non-piezoelectric layer 112.

The design of the PEMS 100 combines a piezoelectric unimorph cantilever with optimal actuation and sensing, as well as a mass-detection-sensitivity-enhancing non-piezoelectric tip 114. The miniaturization of the cantilevers uses highly piezoelectric layers on the order of micron thickness. The benefits of non-piezoelectric tip 114 are nontrivial. The benefits of non-piezoelectric tip 114 can be seen from a comparison of piezoelectric micro-cantilever sensors (PEMS) 100 of various tip lengths and thicknesses. Solving the fourth order differential flexural wave equation of the cantilever developed a transcendental equation, discussed below in example 1. The transcendental equation permits accurate prediction of the appropriate non-piezoelectric tip 114 length and thickness for optimal sensitivity and Q-factor. Alternatively, this calculation can also be used calculate the optimal length and thickness for the piezoelectric layer in embodiments where a piezoelectric tip is being employed.

EXAMPLE 1

FIGS. 4-8$f$ show various graphs that demonstrate the performance of PECS 15, and the effects of variations in the length of non-piezoelectric tip 14. PECS 15 detects mass changes by electrically monitoring resonance frequency shifts in flexural modes. The measured resonance frequencies range from 500 kHz to 1500 kHz, or from 1 kHz to 1000 kHz.

Figure 4:
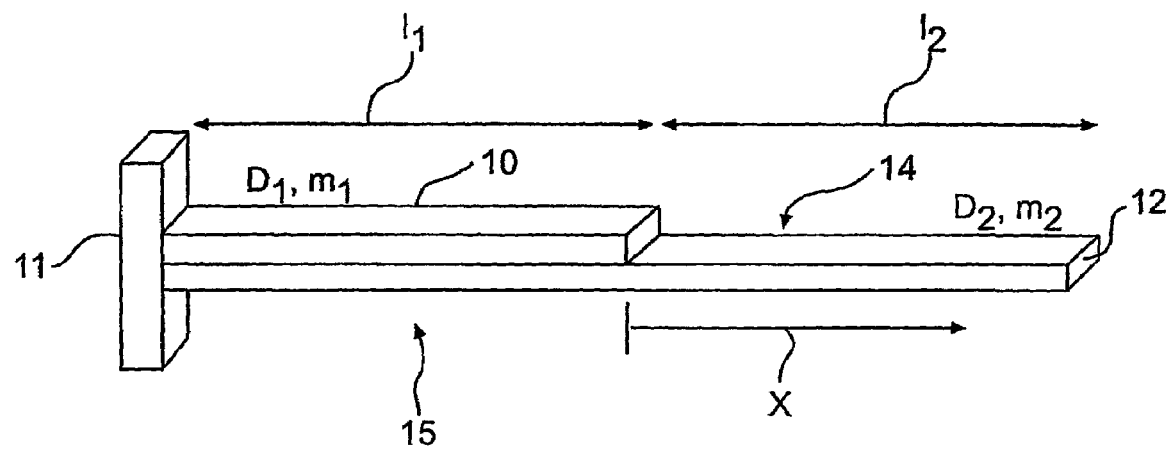
FIG. 4 shows a diagram of a piezoelectric cantilever sensor illustrating the parameters used in determining the geometry of the piezoelectric cantilever sensor.

FIG. 4 shows a diagram of PECS 15 illustrating the parameters used in determining the geometry of PECS 15. The equation $$D_i \frac{d^4 h_i(x,t)}{dx^4} + m_i \frac{d^2 h_i(x,t)}{dt^2} = 0, i = 1, \text{ or } 2$$

governs the waveform for of PECS 15. The equation:

$$h_1(x) = C_{11}\sin(k_1 x) + C_{12}\cos(k_1 x) + C_{13}\sinh(k_1 x) + C_{14}\cosh(k_1 x)$$

governs that portion of PECS 15 that extends for length $l_1$ and contains both piezoelectric layer 10 and non-piezoelectric layer 12, while the equation:

$$h_2(x) = C_{21}\sin(k_2 x) + C_{22}\cos(k_2 x) + C_{23}\sinh(k_2 x) + C_{24}\cosh(k_2 x)$$

governs that portion of non-piezoelectric layer 12 that begins at the end of $l_1$ and extends the length of $l_2$.

Figure 5:
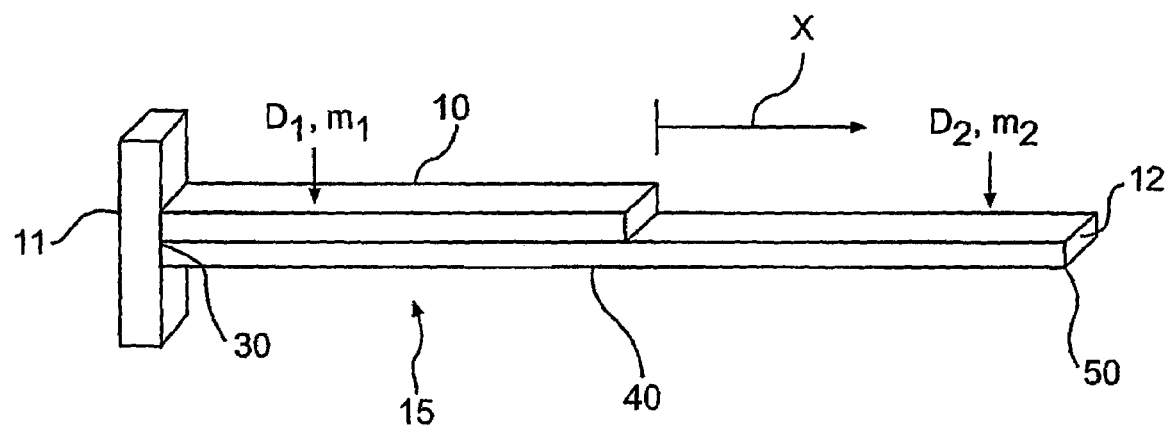
FIG. 5 shows a diagram of a piezoelectric cantilever sensor illustrating the locations of various points on the piezoelectric cantilever sensor where specific equations govern the boundary conditions.

FIG. 5 shows the equations governing the boundary conditions for the various points on PECS 15. At clamp end 30, displacement equals 0, slope equals 0, and $x = -l_1$. At continuation point 40, $x = 0$, therefore, displacement is $h_1(0) = h_2(0)$, slope is $$\left.\frac{dh_1(x)}{dx}\right|_{x=0} = \left.\frac{dh_2(x)}{dx}\right|_{x=0},$$

bending moment is $$\left.D_1 \frac{d^2 h_1(x)}{dx^2}\right|_{x=0} = \left.D_2 \frac{d^2 h_2(x)}{dx^2}\right|_{x=0},$$

and axial force is $$\left.D_1 \frac{d^3 h_1(x)}{dx^3}\right|_{x=0} = \left.D_2 \frac{d^3 h_2(x)}{dx^3}\right|_{x=0}.$$

At free end 50, $x = l_2$, the slope is $$\left.D_2 \frac{d^2 h_2(x)}{dx^2}\right|_{x=l_2} = 0,$$

and the axial force is $$\left.D_2 \frac{d^3 h_2(x)}{dx^3}\right|_{x=l_2} = 0.$$

The waveform equation and the boundary conditions are used to give the transcendental equation shown below:

$$\left\{\frac{\begin{array}{l}[b(1-ab^2)\sinh(k_2 l_2) - b(1+ab^2)\sin(k_2 l_2)] \\ [\sinh(k_1 l_1)\cos(k_1 l_1) + \cosh(k_1 l_1)\sin(k_1 l_1)] + \\ [(1-ab^2)\cosh(k_2 l_2) - (1+ab^2)\cos(k_2 l_2)] \\ [\sinh(k_1 l_1)\sin(k_1 l_1) - \cosh(k_1 l_1)\cos(k_1 l_1)] + \\ [(1+ab^2)\cosh(k_2 l_2) - (1-ab^2)\cos(k_2 l_2)]\end{array}}{\begin{array}{l}[b(1-ab^2)\sinh(k_2 l_2) - b(1+ab^2)\sin(k_2 l_2)] \\ [\sinh(k_1 l_1)\sin(k_1 l_1) + \cosh(k_1 l_1)\cos(k_1 l_1)] + \\ [(1-ab^2)\cosh(k_2 l_2) - (1+ab^2)\cos(k_2 l_2)] \\ [\cosh(k_1 l_1)\sin(k_1 l_1) - \sinh(k_1 l_1)\cos(k_1 l_1)] + \\ [b(1-ab^2)\sin(k_2 l_2) - b(1+ab^2)\sinh(k_2 l_2)]\end{array}}\right\} =$$

$$\left\{\begin{array}{l}[b(1-ab^2)\cosh(k_2 l_2) - b(1+ab^2)\cos(k_2 l_2)] \\ [\sinh(k_1 l_1)\cos(k_1 l_1) + \cosh(k_1 l_1)\sin(k_1 l_1)] + \\ [(1-ab^2)\sinh(k_2 l_2) + (1+ab^2)\sin(k_2 l_2)] \\ [\sinh(k_1 l_1)\sin(k_1 l_1) - \cosh(k_1 l_1)\cos(k_1 l_1)] + \\ [(1+ab^2)\sinh(k_2 l_2) + (1-ab^2)\sin(k_2 l_2)] \\ \hline [b(1-ab^2)\cosh(k_2 l_2) - b(1+ab^2)\cos(k_2 l_2)] \\ [\sinh(k_1 l_1)\sin(k_1 l_1) + \cosh(k_1 l_1)\cos(k_1 l_1)] + \\ [(1-ab^2)\sinh(k_2 l_2) + (1+ab^2)\sin(k_2 l_2)] \\ [\cosh(k_1 l_1)\sin(k_1 l_1) - \sinh(k_1 l_1)\cos(k_1 l_1)] + \\ [b(1-ab^2)\cos(k_2 l_2) - b(1+ab^2)\cosh(k_2 l_2)]\end{array}\right\}$$

With $$f_j = k_{i,j}^2 \sqrt{\frac{D_i}{m_i}}$$

and i=section 1, or 2, and j=the j'th mode. This becomes $$\frac{k_{1,j}}{k_{2,j}} = \sqrt[4]{\frac{D_2}{D_1} \cdot \frac{m_1}{m_2}}$$

with $$\frac{D_1}{D_2} = a$$

and $$\frac{k_1}{k_2} = b.$$

Figure 6:
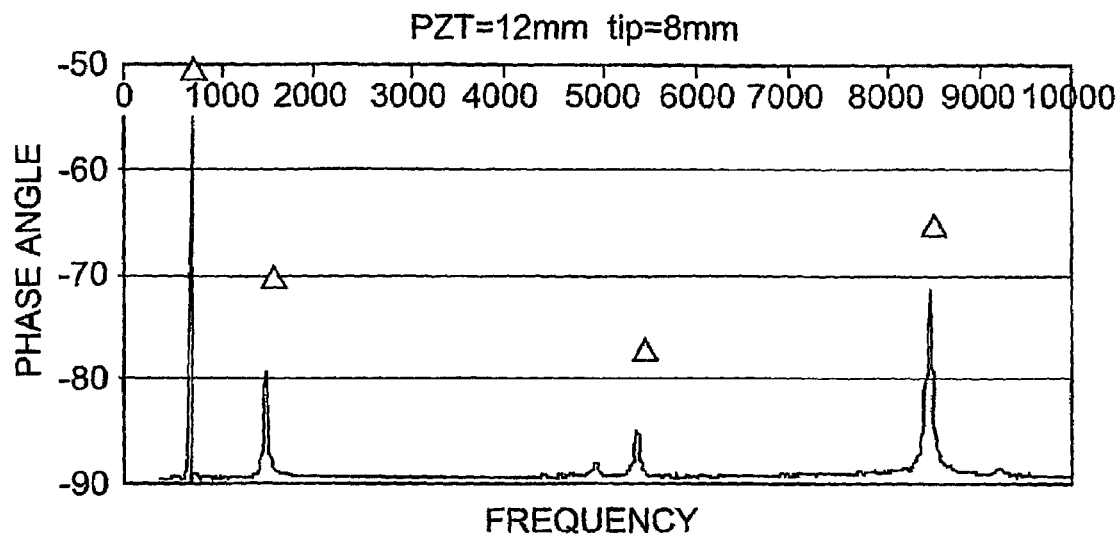
FIG. 6 shows a graph depicting the experimental data for a piezoelectric cantilever sensor compared to theoretically calculated values.

FIG. 6 shows the experimental data for a PECS 15 with a piezoelectric layer 10 that is 12 mm. in length and a non-piezoelectric tip 14 of 8 mm. in length. FIG. 6 shows the actual frequency measured and the triangles illustrate theoretical values for the wave frequency. From this graph it is demonstrated that the theoretical values match the experimental data very closely.

Figure 7:
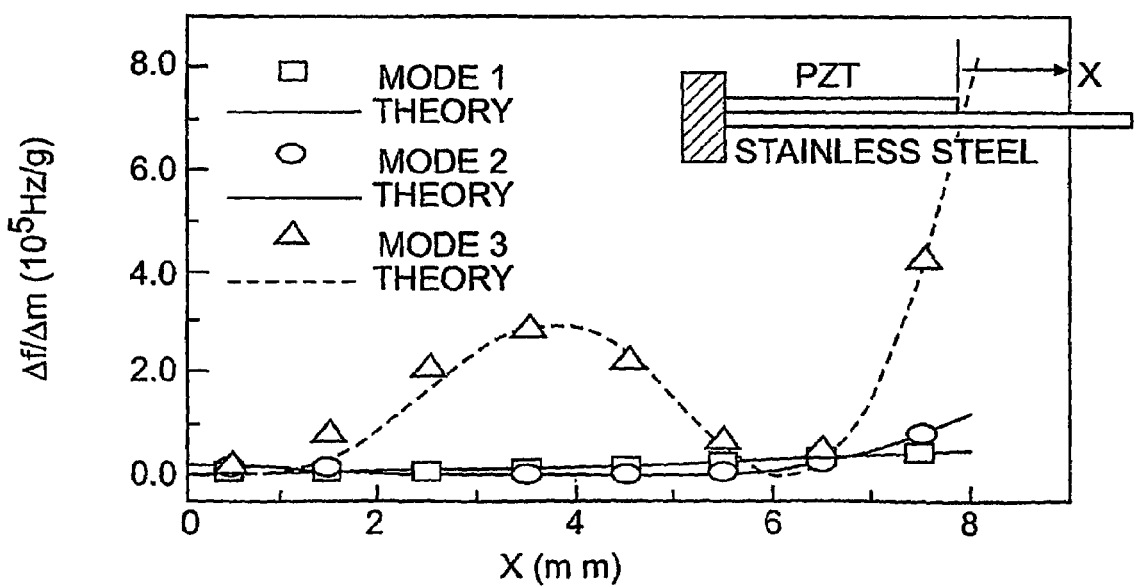
FIG. 7 shows a graph depicting the sensitivity of a piezoelectric cantilever sensor for different modes.

FIG. 7 demonstrates the sensitivity of the PECS 15 for different modes. The real amplitudes of each mode are not known, however it is known that the lower mode will give a much larger displacement.

$$\frac{df}{dm}\bigg|_{l_2} = \frac{f}{M_{eff}}$$

is the equation that indicates sensitivity, i.e. the amount of mass that PECS 15 can detect given the geometry of the example provided. In FIG.

$$\frac{df}{dm} = 6.18 \times 10^4 \text{Hz/g.}$$

Hz/g for mode 1. For mode 2, $$\frac{df}{dm} = 1.28 \times 10^5 \text{Hz/g.}$$

For mode 3, $$\frac{df}{dm} = 5.51 \times 10^5 \text{Hz/g.}$$

Figure 8A:
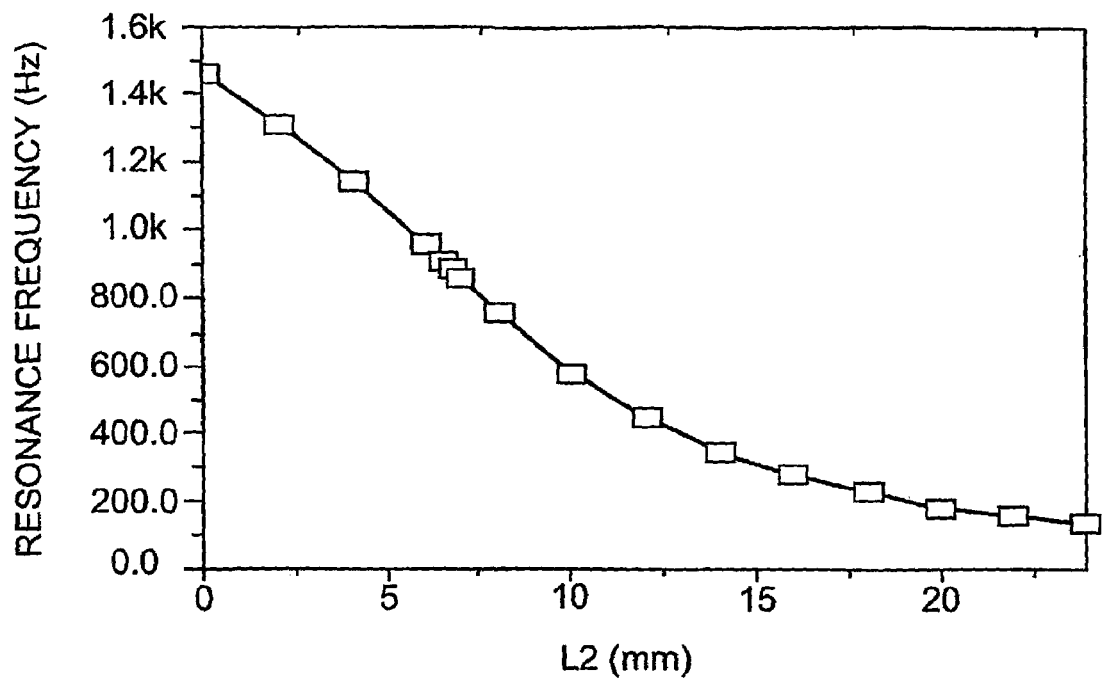
FIG. 8a shows the graph for mode 1 demonstrating the change in resonance frequency relative to the length of a non-piezoelectric tip.

FIG. 8a shows the change in resonance frequency of a PECS 15 as the length of non-piezoelectric tip 14 varies for mode 1. PECS 15 has a piezoelectric layer 10 that is 0.254 mm. thick and a non-piezoelectric layer 12 that is 0.1 mm. thick. The length ($l_1$) of piezoelectric layer 10, remains constant at 12 mm. The length ($l_2$) of non-piezoelectric tip 14, varies from 0 mm. to 24 mm, in order to show the effect of varying the length of non-piezoelectric layer 10.

Figure 8B:
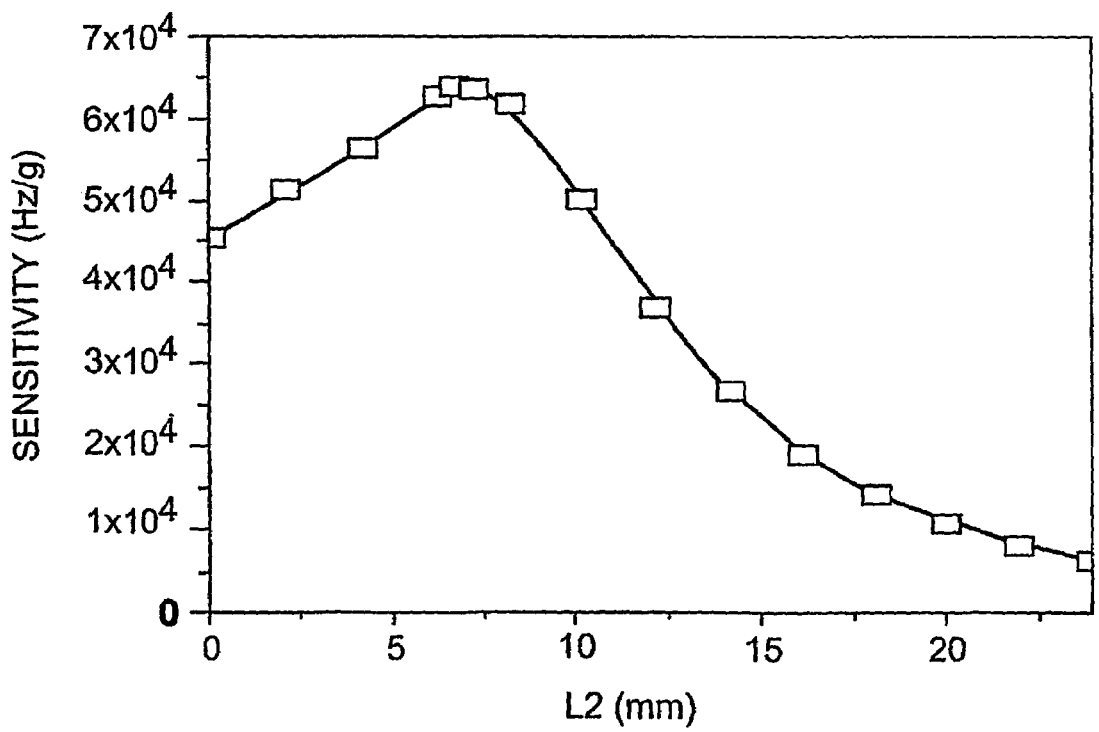
FIG. 8b shows the graph for mode 1 demonstrating the change in sensitivity relative to the length of a non-piezoelectric tip
Figure 8C:
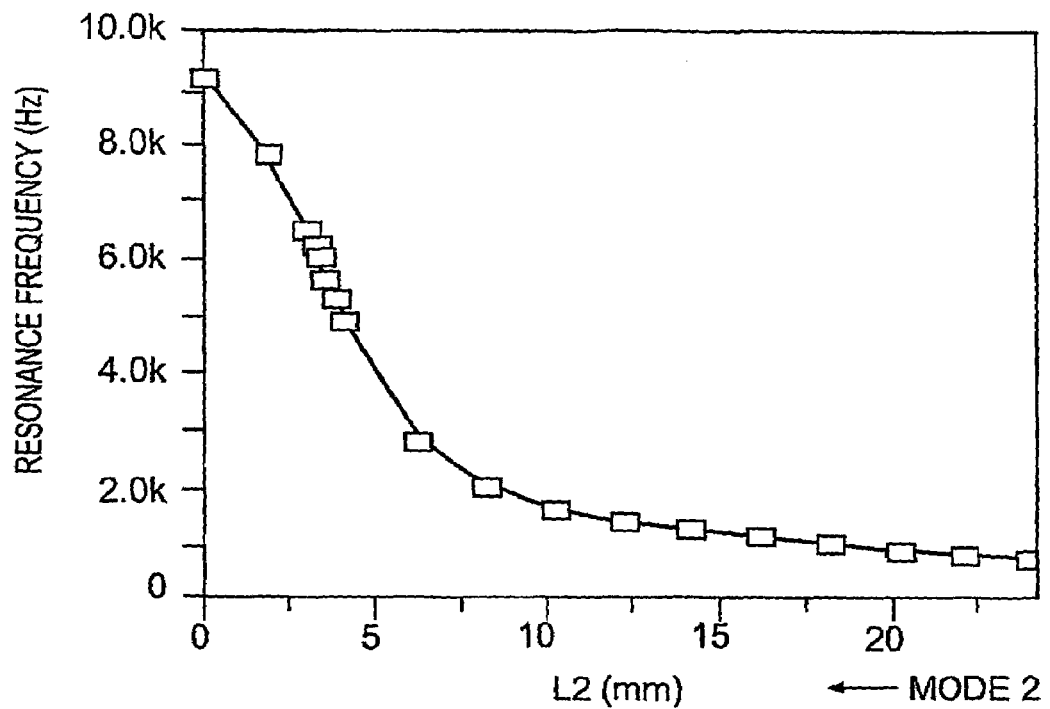
FIG. 8c shows the graph for mode 2 demonstrating the change in resonance frequency relative to the length of a non-piezoelectric tip.
Figure 8D:
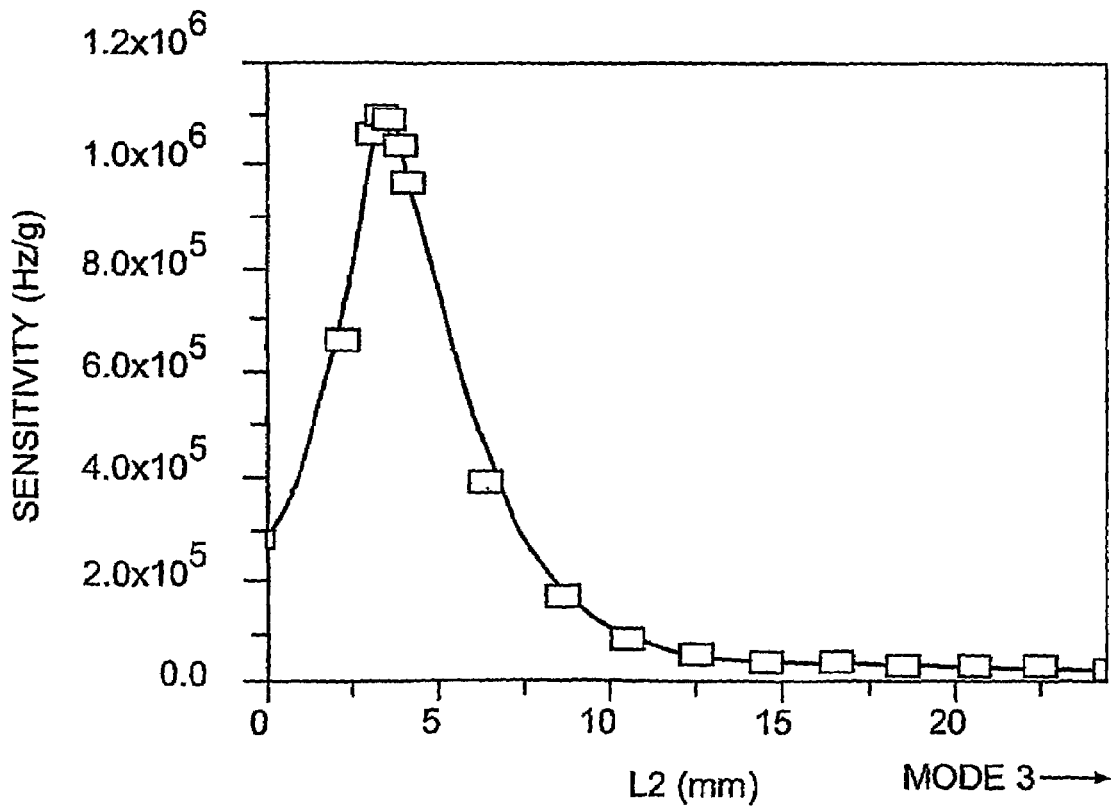
FIG. 8d shows the graph for mode 2 demonstrating the change in sensitivity relative to the length of a non-piezoelectric tip.
Figure 8E:
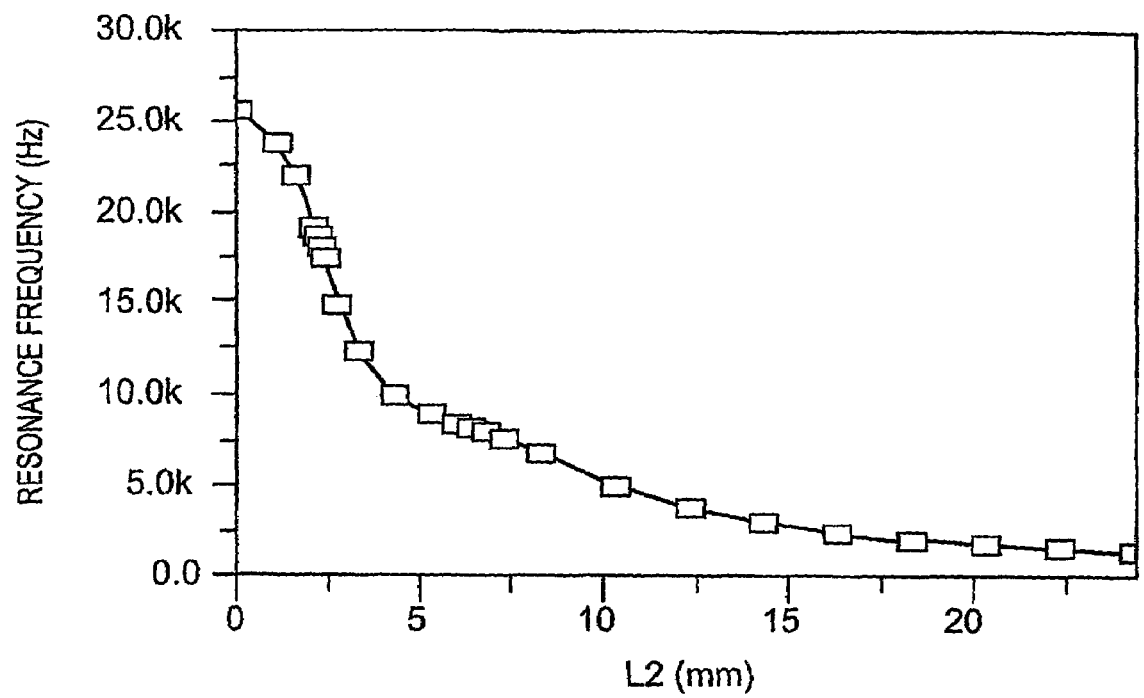
FIG. 8e shows the graph for mode 3 demonstrating the change in resonance frequency relative to the length of a non-piezoelectric tip.
Figure 8F:
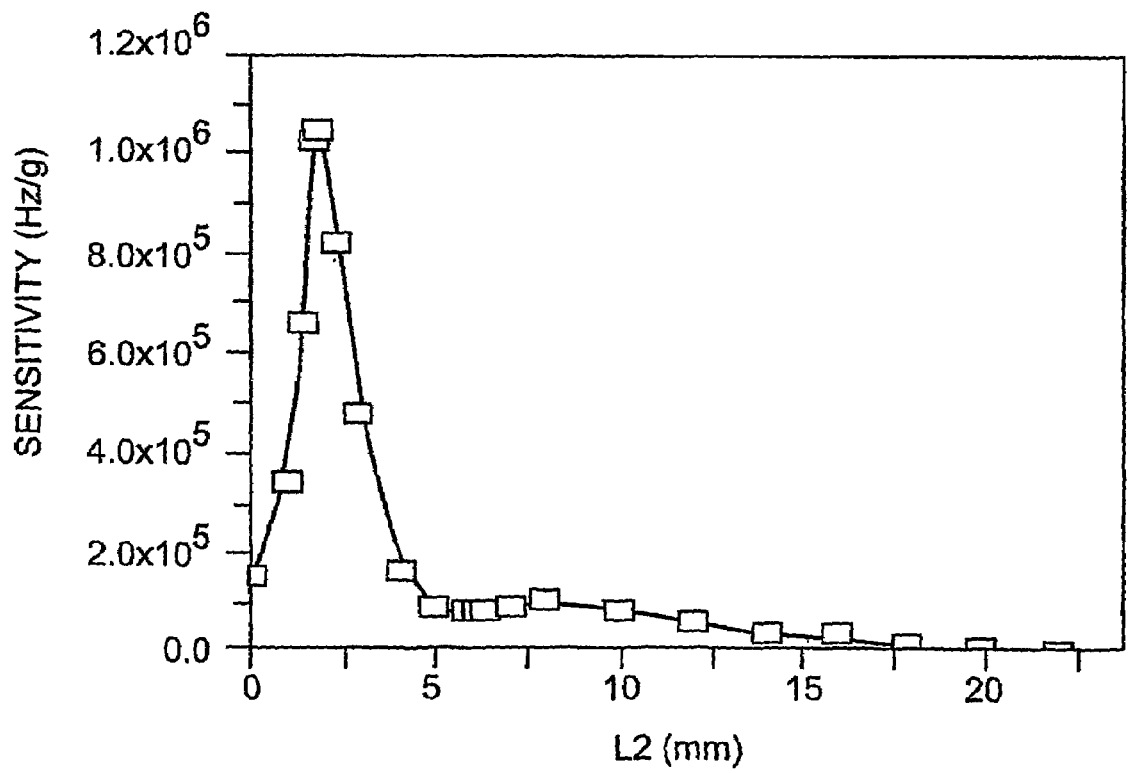
FIG. 8f shows the graph for mode 3 demonstrating the change in sensitivity relative to the length of a non-piezoelectric tip.

FIG. 8b shows the sensitivity of PECS 15 as the length of non-piezoelectric tip 14 is varied for mode 1. From this graph it can be seen that there is a point where the sensitivity is greatest. FIG. 8c shows a graph for mode 2 demonstrating the change in resonance frequency relative to the length of non-piezoelectric tip 14. FIG. 8d shows a graph for mode 2 demonstrating the change in sensitivity relative to the length of non-piezoelectric tip 14. FIG. 8e shows graphs for mode 3 demonstrating the change in resonance frequency relative to the length of non-piezoelectric tip 14. FIG. 8f shows a graph for mode 2 demonstrating the change in sensitivity relative to the length of non-piezoelectric tip 14. From these graphs it can be seen that with a non-piezoelectric tip 14 length of 2 mm, a very high sensitivity can be obtained for PECS 15.

EXAMPLE 2

Figure 9:
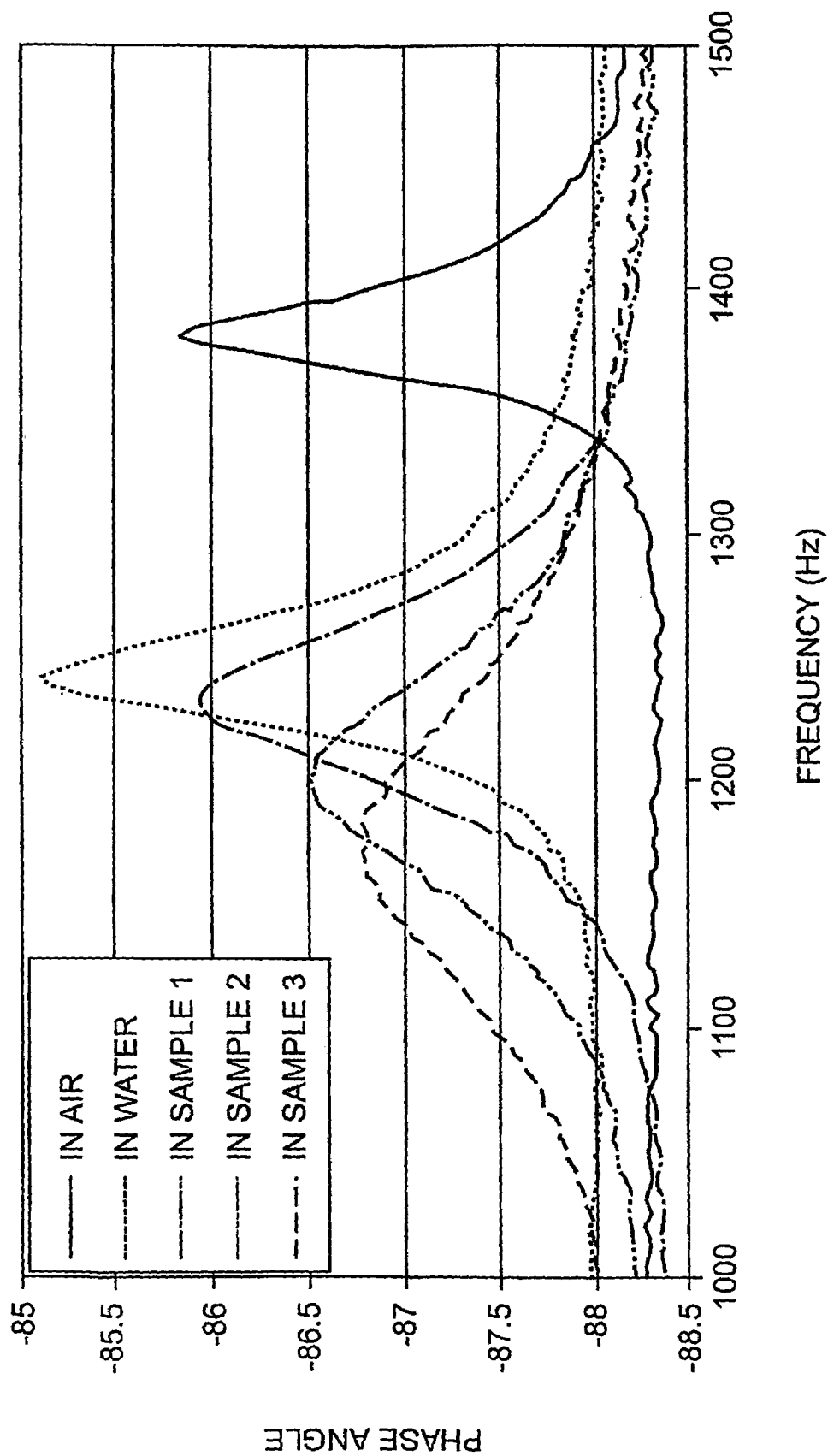
FIG. 9 shows the resonance spectra of PECS in air, water, and sample liquids.

This example shows the behavior of PECS 15 in three viscous solutions labeled as samples 1-3 in FIG. 9, as well as in air and water. This example demonstrates that the viscosity of the fluid in which PECS 15 is immersed, does not dramatically affect the resonance frequency. Therefore, PECS 15 will be useful for detection in viscous solutions. Furthermore, the ability to predict the behavior of the PECS 15 in various viscosities based upon the known geometry of PECS 15 permits the use of PECS 15 to measure the viscosity of a fluid. The viscosity of the three samples was measured by a rheometer. The viscosity of water and the three samples are, shown below in Table 1.

TABLE 1

|  | Viscosity (cp) | Δf (Hz) | Q value | Δf/$f_{air}$(%) |
| --- | --- | --- | --- | --- |
| Water | 1 | 140 | 17.5 | 10.1 |
| Sample 1 | 249 | 180 | 11.6 | 13 |
| Sample 2 | 995 | 230 | 7.4 | 17 |
| Sample 3 | 3700 | 280 | 5.6 | 20.3 |

Q=f/δf, with f representing the resonance frequency, and δf representing the width of the resonance peak at half the peak height. A higher Q value indicates a better signal intensity. From Table 1 it can be seen that even in sample 3, with a viscosity measurement of 3700 (cp), PECS 15 has a better signal intensity than a silicon-based micro-cantilever, which has a Q value of about 1 in water. It can further be seen that viscosity-induced change in resonance frequency is easily measured, thereby making it possible to employ measurements of the resonance frequency to determine the viscosity of a liquid or gas. The frequency for viscosity sensing ranges from about 100 Hz to 1500 kHz, and is preferably 1100 Hz to 1000 kHz.

It is to be understood, that even though numerous characteristics and advantages of the present invention have been set forth in the foregoing description, together with details of the structure and function of the invention, the disclosure is illustrative only, and changes may be made in detail, especially in matters of shape, size, choice of materials and arrangement of parts within the principles of the invention to the full extent indicated by the broad general meaning of the terms in which the appended claims are expressed.

What is claimed is:

1. An apparatus for sensing mass comprising:
    a non-piezoelectric layer;
    a piezoelectric layer bonded to said non-piezoelectric layer, wherein a length of one of said piezoelectric layer and said non-piezoelectric layer is less than a length of another of said piezoelectric layer and non-piezoelectric layer, wherein a ratio of a thickness of said non-piezoelectric layer to a thickness of said piezoelectric layer is from about 0.1 to about 3.0; and
    electrodes located proximate to said piezoelectric layer.

2. The apparatus of claim 1, wherein said non-piezoelectric layer comprises a material selected from the group consisting of ceramics, metals, polymers and composites one or more of ceramics, metals, and polymers.

3. The apparatus of claim 2, wherein said non-piezoelectric layer comprises a material selected from the group consisting of: silicon dioxide, copper, stainless steel, and titanium.

4. The apparatus of claim 1, wherein said piezoelectric layer comprises a piezoelectric material selected from the group consisting of lead zirconate titanate, lead magnesium niobate-lead titanate solid solutions, and strontium lead titanate.

5. The apparatus of claim 1, further comprising a bonding pad.

6. The apparatus of claim 5, wherein said bonding pad is made from a material selected from the group consisting of gold, $SiO_2$, a material capable of immobilization of a receptor material, and an absorbent material appropriate for use in chemical sensing.

7. The apparatus of claim 1, wherein said non-piezoelectric layer has a length of about 2.5 centimeters to about 0.5 microns.

8. The apparatus of claim 1, wherein said non-piezoelectric layer has a length of about 1.5 centimeters to about 1.0 microns.

9. The apparatus of claim 1, wherein said piezoelectric layer has a length of about 2.5 centimeters to about 0.5 microns.

10. The apparatus of claim 1, wherein said piezoelectric layer has a length of about 1.5 centimeters to about 1.0 microns.

11. The apparatus of claim 1, wherein said electrodes are employed to measure resonance frequency.

12. The apparatus of claim 11, wherein the presence of mass is determined by measurement of a shift in resonance frequency.

13. The apparatus of claim 11, wherein the resonance frequency when sensing mass is from about 1 kHz to about 10 MHz.

14. The apparatus of claim 11, wherein the resonance frequency when sensing mass is from about 50 kHz to about 5 MHz.

15. The apparatus of claim 1, wherein said piezoelectric layer is triangular in shape.

16. The apparatus of claim 1, wherein said piezoelectric layer is round in shape.

17. The apparatus of claim 1, wherein at least one of said piezoelectric layer and said non-piezoelectric layer is tapered.

18. The apparatus of claim 1, wherein a dimension of said non-piezoelectric layer is less than a corresponding dimension of said piezoelectric layer.

19. The apparatus of claim 1, wherein one of said electrodes is located between said non-piezoelectric layer and said piezoelectric layer.

20. The apparatus of claim 1, further comprising a second piezoelectric layer located on a side of said non-piezoelectric layer opposite a side on which said first piezoelectric layer is located.

21. The apparatus of claim 1, wherein the piezoelectric layer thickness ranges from about 250 µm to about 0.5 µm.

22. A method for the detection of mass comprising the steps of:
    providing a sensing apparatus comprising;
    a non-piezoelectric layer; and
    a piezoelectric layer bonded to said non-piezoelectric layer, wherein a length of one of said piezoelectric layer and said non-piezoelectric layer is less than a length of another of said piezoelectric layer and non-piezoelectric layer;
    measuring a resonance frequency of said apparatus; and
    comparing said measured resonance frequency to a baseline resonance frequency to determine a frequency shift wherein a ratio of a thickness of said non-piezoelectric layer to a thickness of said piezoelectric layer is from about 0.1 to about 3.0.

23. The method of claim 22, wherein said apparatus further comprises electrodes located proximate to said piezoelectric layer.

24. The method of claim 22 further comprising the step of: determining the presence of a biological or chemical substance based upon said determined shift in resonance frequency.

25. The method of claim 22, further comprising the step of providing more than one sensing apparatus to form an array.

26. The method of claim 22, wherein said step of measuring resonance frequency measures frequencies of about 1 kHz to about 10 MHz.

27. The method of claim 22, wherein said step of measuring resonance frequency measures frequencies of about 50 kHz to about 5 MHz.

28. The method of claim 22, wherein said non-piezoelectric layer has a length of from about 2.5 centimeters to about 0.5 microns.

29. The method of claim 22, wherein said non-piezoelectric layer has a length of from about 1.5 centimeters to about 1.0 micron.

30. The method of claim 22, wherein said piezoelectric layer has a length of from about 2.5 centimeters to about 0.5 microns.

31. The method of claim 22, wherein said piezoelectric layer has a length of from about 1.5 centimeter to about 1.0 micron.

32. The method of claim 22, wherein said piezoelectric layer comprises at least one material selected from the group consisting of: lead zirconate titanate, lead magnesium niobate-lead titanate solid solutions and strontium lead titanate.

33. The method of claim 22, wherein said step of measuring occurs in a liquid with a viscosity greater than water.

34. The method of claim 22, wherein said step of measuring occurs in a liquid with a viscosity of from about 1 cp. to about 4000 cp.

35. The method of claim 22, further comprising the step of determining a mass of a biological or chemical substance based upon said determined shift in resonance frequency.

36. The method of claim 22, wherein a ratio of a thickness of said non-piezoelectric layer to a thickness of said piezoelectric layer is from about 0.2 to about 1.0.

37. The method of claim 22, wherein the piezoelectric layer thickness ranges from about 250 µm to about 0.5 µm.

38. A method for measuring viscosity comprising the steps of:
- providing an apparatus comprising;
- a non-piezoelectric layer;
- a piezoelectric layer bonded to said non-piezoelectric layer, wherein a length of one of said piezoelectric layer and said non-piezoelectric layer is less than a length of another of said piezoelectric layer and said non-piezoelectric layer; and electrodes located proximate to said piezoelectric layer;
- placing said apparatus in a liquid;
- measuring a resonance frequency of said apparatus;
- comparing the measured resonance frequency to a baseline to determine a shift in resonance frequency; and
- determining viscosity of said liquid based upon said determined shift in resonance frequency wherein a ratio of a thickness of said non-piezoelectric layer to a thickness of said piezoelectric layer is from about 0.1 to about 3.0.

39. The method of claim 38, wherein said step of measuring resonance frequency measures frequencies of about 100 Hz to about 1500 kHz.

40. The method of claim 38, wherein said step of measuring resonance frequency measures frequencies of about 1100 Hz to about 1000 kHz.

41. The method of claim 38, wherein a ratio of a thickness of said non-piezoelectric layer to a thickness of said piezoelectric layer is from about 0.2 to about 1.0.

42. The method of claim 38, wherein the piezoelectric layer thickness ranges from about 250 µm to about 0.5 µm.

43. The method of claim 38, wherein one of said electrodes is located between said non-piezoelectric layer and said piezoelectric layer.

* * * * *